United States Patent [19]
Shefet

[11] Patent Number: 5,546,849
[45] Date of Patent: Aug. 20, 1996

[54] HYDROSTATIC HEATING APPARATUS

[75] Inventor: Sarid M. Shefet, Raleigh, N.C.

[73] Assignee: North Carolina State University, Raleigh, N.C.

[21] Appl. No.: 399,201

[22] Filed: Mar. 6, 1995

[51] Int. Cl.$^6$ .................. A23L 3/16; A23L 3/22
[52] U.S. Cl. .................. 99/330; 99/356; 99/403; 99/470; 99/477; 99/483
[58] Field of Search .................. 99/331, 330, 356, 99/359–365, 366, 367, 403, 370, 470, 483, 484, 492, 516, 534–536; 132/133, 145, 152; 134/132; 422/292, 297, 307, 308, 304, 20; 426/232, 405–407, 522, 524, 520, 521, 511, 509, 510, 523

[56] References Cited

U.S. PATENT DOCUMENTS

| | | | |
|---|---|---|---|
| 3,793,939 | 3/1974 | Wieser et al. | 99/483 |
| 3,818,818 | 6/1974 | Hice, Sr. . | |
| 3,927,976 | 12/1975 | Reimers et al. | 422/296 |
| 4,059,919 | 11/1977 | Green . | |
| 4,110,481 | 8/1978 | Albright et al. . | |
| 4,181,072 | 1/1980 | Hirahara . | |
| 4,385,035 | 5/1983 | Akitoshi et al. | 422/297 |
| 4,543,263 | 9/1985 | Goldhahn | 426/520 |
| 4,547,383 | 11/1985 | Goldhahn . | |
| 4,604,948 | 8/1986 | Goldhahn | 99/470 |
| 4,830,865 | 5/1989 | McFarlane et al. . | |
| 4,863,377 | 9/1989 | Gaignoux et al. | 432/133 |
| 4,929,463 | 5/1990 | Meyer . | |
| 4,962,700 | 10/1990 | Skobic et al. | 99/361 X |
| 5,049,400 | 9/1991 | Hayden | 422/20 X |
| 5,143,199 | 9/1992 | Evans | 99/360 |
| 5,161,457 | 11/1992 | Evans | 99/362 X |
| 5,199,346 | 4/1993 | Hadley et al. | 99/477 |
| 5,215,002 | 6/1993 | Veltman | 134/132 X |
| 5,275,091 | 1/1994 | McFarlane et al. . | |
| 5,301,603 | 4/1994 | Mignogna | 99/359 |

FOREIGN PATENT DOCUMENTS

| | | |
|---|---|---|
| 1282003 | 7/1972 | Switzerland . |
| 1759338A1 | 9/1992 | U.S.S.R. . |
| 2264037 | 8/1993 | United Kingdom . |

*Primary Examiner*—Timothy F. Simone
*Attorney, Agent, or Firm*—Bell, Seltzer, Park & Gibson

[57] ABSTRACT

A hydrostatic heating apparatus comprises an enclosed chamber which is open to atmospheric pressure and contains the hydrostatic liquid. The enclosed chamber has a product inlet opening and a product outlet opening and also has a heating zone positioned between the product inlet opening and the product outlet opening. The apparatus has a transporting device such as a conveyor positioned in the enclosed chamber which extends through the heating zone for transporting the particulate product in the liquid from the product inlet opening through the heating zone to the product outlet opening. The apparatus maintains the particulate product in the liquid under hydrostatic pressure in the heating zone. The apparatus may be used in combination with an aseptic packager connected to the enclosed chamber product outlet opening for aseptically packaging the particulate product.

20 Claims, 6 Drawing Sheets

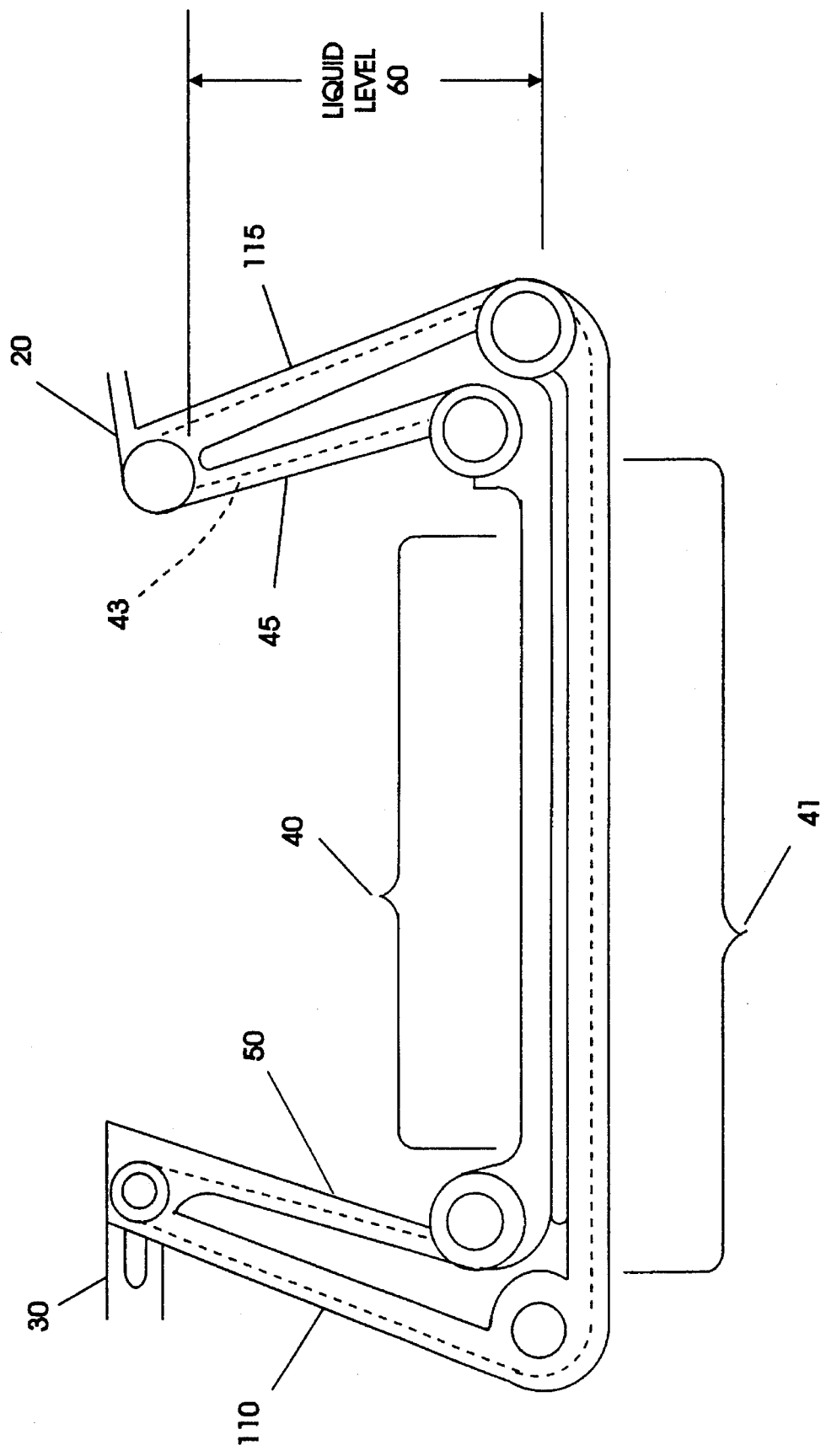

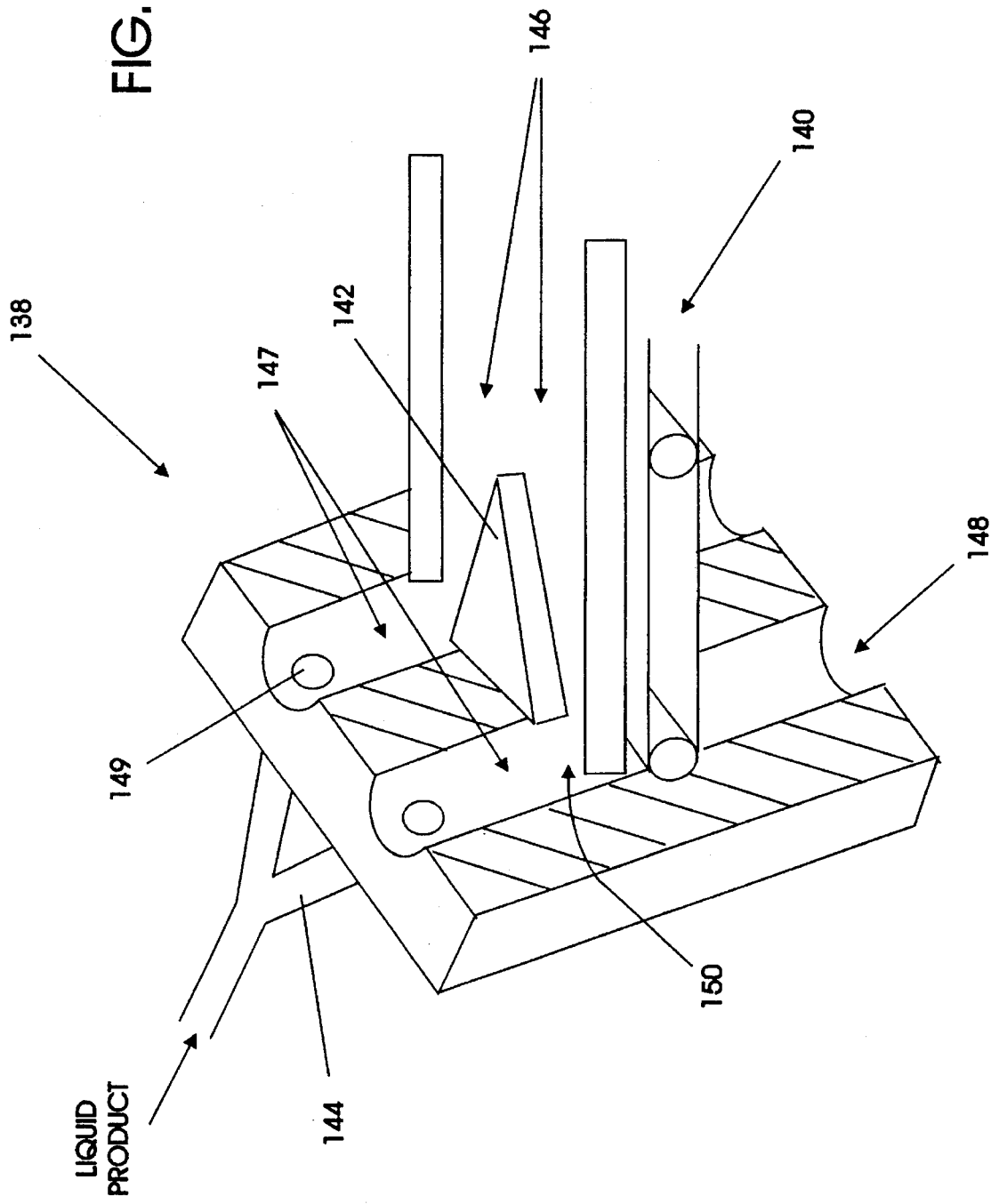

FIG. 9A
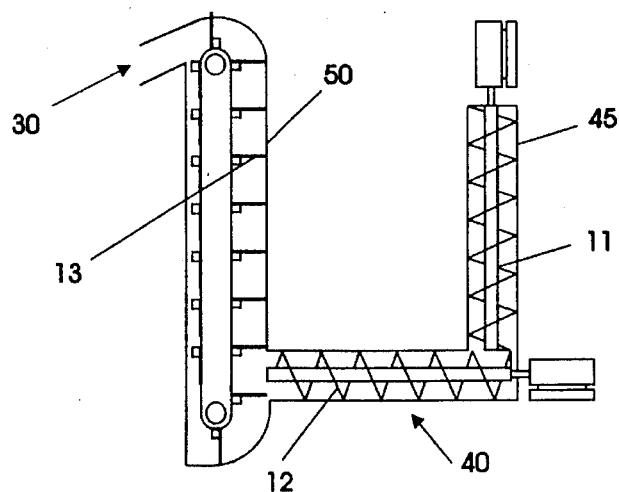
FIG. 9B
FIG. 9C
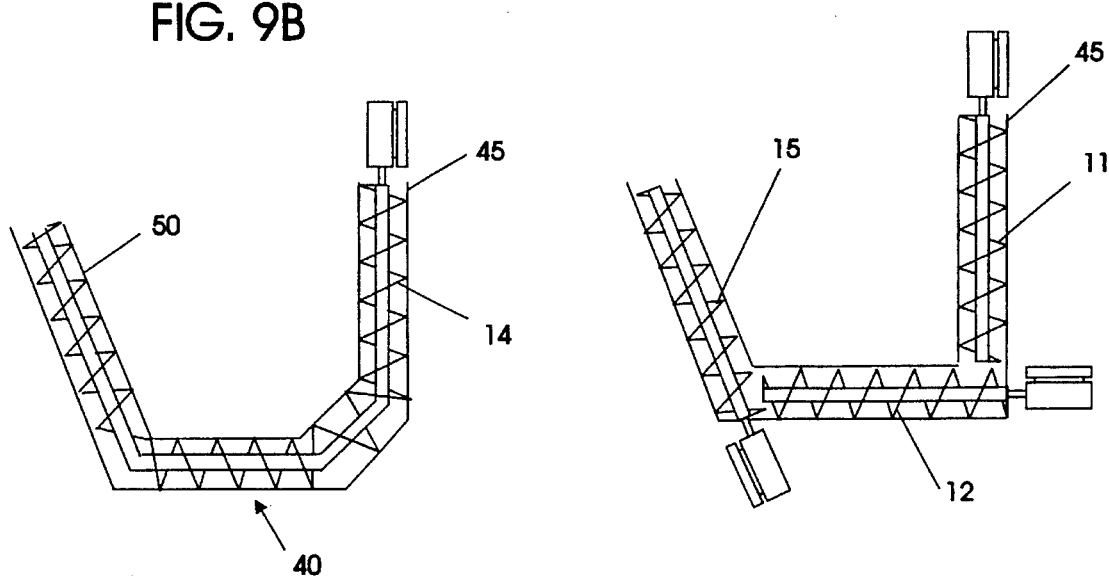

5,546,849

HYDROSTATIC HEATING APPARATUS

FIELD OF THE INVENTION

This invention concerns a method and apparatus for sterilizing a particulate product in which the product is immersed in a column of heated hydrostatic liquid which is open to atmospheric pressure.

BACKGROUND OF THE INVENTION

Aseptic food products are processed by heating the food in a sterile environment at a temperature and time sufficient to kill a reference microorganism population, and thereafter maintaining the sterility during the filling and packaging operations. The unit of measurement, Fo, designates heat treatment of one minute at 121.1 degrees Centigrade referenced to z=10 degrees Centigrade. Another unit of measurement, D, indicates in logrithmic scale, the time of heating, at temperature T, needed to destroy 90% of a designated contaminant population. An Fo equal to 2.45 minutes is a generally accepted minimum design criterion for a 12 D destruction for *Clostridium botulinum*. However, recognizing that spoilage generally occurs due to the survival of heat resistant spore-forming bacteria more resistant than *Clostridium botulinum,* an Fo equal to five minutes has been generally accepted for low acid, aseptically processed and packaged foods. There is a logrithmic relationship between sterilizing time and temperature, therefore the higher the processing temperature, the less processing time is necessary to produce a sterilized product. In addition, there is a product quality advantage in using a higher processing temperature because microorganisms are more temperature sensitive than are many desirable components of food. This advantage is explained by comparing the slope (z) of the thermal death time curve (TDT) with similar curves for desirable components of food such as thiamin, chlorophyll, and ascorbic acid. Thermal death time is the time to achieve sterility of a suspension containing a known number of cells or spores at any predetermined temperature.

Conventional aseptic food processing systems are typically batch based and typically sterilize food in liquid in a closed system. These systems typically heat food particulates and prepackaged products to the requisite times and temperatures by using pumps, elevated pressure enclosures, and heat exchangers. The products are generally placed in a surface heat exchanger or in a sealed chamber and heated in a gaseous environment and pressure cooked. The scrape surface heat exchanger tends to mash, shear, or tear the product which may yield an unacceptable product. In addition, the conventional batch heating systems have processing times which include the batch heating and cooling process times.

A continuous sterilization process which is open to atmospheric pressure reduces both the process time and amount of energy currently needed to run the batch type closed systems. A liquid column increases the boiling point of the liquid in the sterilization zone and allows the product to be both sterilized and cooked while being continuously transported through the heated liquid to the aseptic zone. The liquid in the sterilization zone acts as a barrier to the aseptic zone. In addition, the integrity and texture of the product is preserved by the reduced processing time. The increased temperature and reduced process time will improve the shelf-life, safety, and nutritional aspects of the sterilized product.

SUMMARY OF THE INVENTION

A first aspect of the present invention is a hydrostatic heating apparatus for heating a particulate product in a liquid. The hydrostatic heating apparatus comprises an enclosed chamber which is open to atmospheric pressure and contains the hydrostatic liquid. The enclosed chamber has a product inlet opening and a product outlet opening and also has a heating zone that may serve as an aseptic heating zone positioned between the product inlet opening and the product outlet opening. The apparatus also comprises a transporting apparatus positioned in the enclosed chamber which extends through the heating zone for transporting the particulate product in the liquid from the product inlet opening through the heating zone to the product outlet opening. The apparatus also comprises a hydrostatic pressure apparatus operatively associated with the enclosed chamber for maintaining the particulate product in the liquid under pressure in the heating zone. Finally, the apparatus includes a heater connected to the enclosed chamber for heating the particulate product in the liquid under pressure in the heating zone.

A second aspect of the present invention is a combination heating and packaging apparatus comprising a hydrostatic heating apparatus as given above and with an aseptic packager connected to the enclosed chamber product outlet opening for aseptically packaging the particulate product.

A third aspect of the invention is a method for the continuous heat-treatment of a particulate product. The method comprises the steps of: (a) providing a liquid column which is open to atmospheric pressure, where the liquid column has an upper portion and a lower portion, the upper portion having a volume sufficient to increase the boiling point of the liquid in the lower portion by a predetermined amount; (b) heating the liquid in the liquid column lower portion to a temperature sufficient to heat the particulate product; and (c) continuously passing the particulate product through the liquid column lower portion with the particulate product directly contacting the liquid.

The foregoing and other objects and aspects of the present invention are described in greater detail in the drawings herein and the specification set forth below.

BRIEF DESCRIPTION OF THE DRAWINGS

FIG. 5 shows an alternative embodiment of the transporting means;

FIG. 8 is a perspective view of an aseptic mixer; and

FIGS. 9A–C is a schematic illustration of alternative embodiments of the transporting means.

DETAILED DESCRIPTION OF THE PREFERRED EMBODIMENTS

Figure 1:
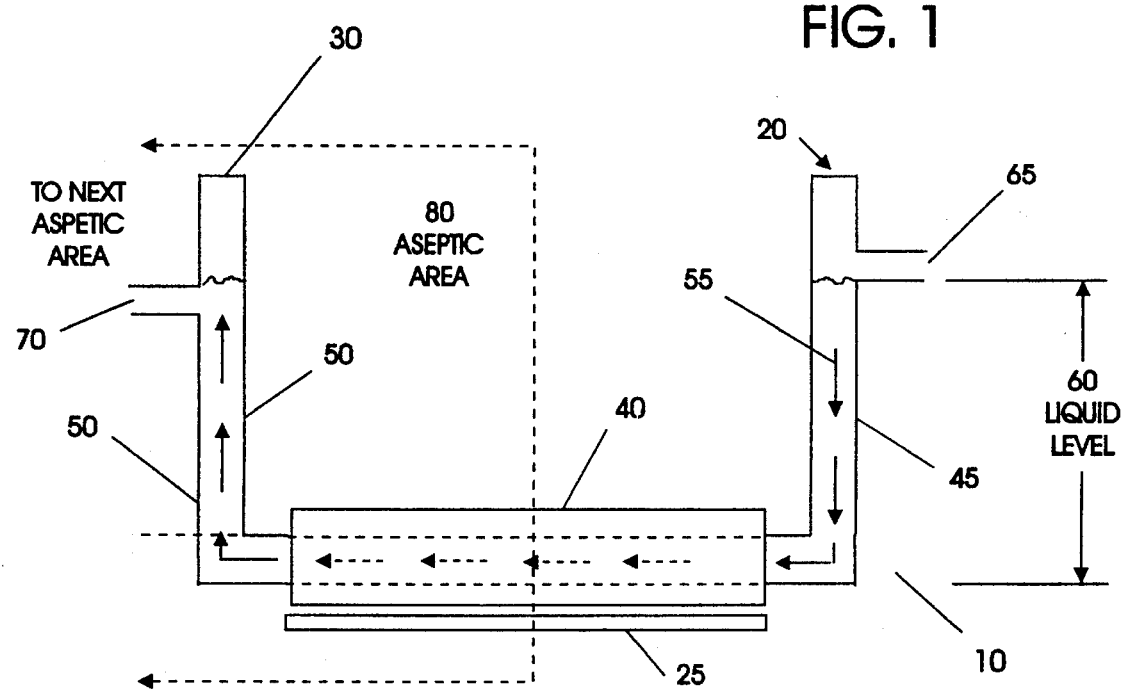
FIG. 1 is a schematic illustration of a hydrostatic heating apparatus of the present invention.

FIG. 1 shows a continuous hydrostatic heating apparatus for heating a particulate product. Generally described, the apparatus uses either an aqueous or non-aqueous liquid. The aqueous liquid includes water, or a water based solution. The non-aqueous liquid includes edible liquids such as corn oil, olive oil, saffron oil, and cannola oil. The liquid is contained in a column configuration housing which may be open to atmospheric pressure. The hydrostatic pressure increases the pressure on the liquid in the lower part of the column and thereby increases the liquid's boiling point at this location which is designated as the aseptic heating zone 40. A heater 25 is placed at the aseptic heating zone 40 in order to heat the temperature of the liquid to a predetermined level. The heater can directly contact the liquid (FIG. 6) or be placed externally on the enclosed chamber 10. The heater can be a direct heater such as a steam injection heater, or an indirect heater such as a heated surface heater. The aseptic heating zone 40 is of a predetermined length. Since the temperature of the liquid in the aseptic heating zone 40 is heated to a predetermined temperature and the length of the aseptic heating zone 40 is also predetermined, the speed of a transporting means (FIG. 4, FIG. 5, FIG. 10) is adjusted such that it moves the product through the aseptic heating zone 40 at a rate sufficient to cook, pasteurize and/or sterilize the particulate product prior to where the particulate product exits the product outlet opening 30. In the present invention, the term "cooking" refers to heating at any temperature above room temperature, and the term "sterility" indicates that there are no microorganisms present that have public health significance or that are capable of reproducing in the food or other particulate product under normal non-refrigerated conditions of storage and distribution.

Once the product exits the aseptic heating zone 40, it is contained in an aseptic area 80 such that the particulate product is protected from contamination throughout any subsequent handling. In the present invention, the term "aseptic" is interchangeable with sterile. The present invention is used for particulate products which are cooked, pasteurized and/or sterilized by the hydrostatic heating apparatus. Particulate products, in the present invention, include any number of products, semi-solid as well as solid, such as but not limited to, peas, beans, pasta, and immersible medical tools. In yet another alternative, the term particulate product includes the liquid by-product of the particulate. The heating apparatus liquid is preferably sterile upon reaching the outlet opening and therefore can be combined as part of the final aseptic product. Therefore, the term particulate product can also include a liquid by-product of the solid or semi-solid product, such as but not limited to, chicken broth created from heating chicken in the hydrostatic heating apparatus.

The hydrostatic heating apparatus comprises an enclosed chamber 10, with a product inlet opening 20 (FIG. 2 item 20, FIG. 3 item 21), a product outlet opening 30 (FIG. 2 item 31, FIG. 3 item 31), and an aseptic heating zone 40. The apparatus further comprises a transporting means (FIG. 4, FIG. 5), a hydrostatic pressure means, and a heater 25. The apparatus has a drive apparatus which has a minimum of external power sources in order to minimize the number of contamination pathways. Therefore, it is preferable to run all the power from one power source, although it is possible to have a multiplicity of power sources. In the preferred embodiment, the product outlet opening is connected to an aseptic area 80. The product exits the product outlet opening 30 (FIG. 2 item 31, FIG. 3 item 31) and either undergoes further product combinations (FIG. 7, FIG. 8) or is transported to an aseptic packager such that the sterility of the product is maintained.

The hydrostatic pressure means has at least one inlet column 45 and at least one exit column 50 which houses a liquid. As described above, the inlet column 45 is in fluid communication with the exit column 50 through the aseptic heating zone 40. The inlet column 45 and the exit column 50 have vertical drops sufficient to hydrostatically increase the pressure of the liquid in the aseptic heating zone 40. The vertical drop is obtained by configuring the inlet column 45 and the exit column 50 perpendicular to or on an inclined slope from the aseptic heating zone 40 such that the liquid level 60 provides the necessary pressure increase in the aseptic heating zone.

The inlet column 45, the aseptic heating zone 40, and the exit column 50 are preferably configured in an essentially linear configuration so that the transporting means may travel along an essentially linear path. In the most simple configuration as illustrated in FIG. 1 there is only one inlet and exit column. However, it is possible to have more than one of either or both columns positioned on the aseptic heating zone 40 to provide equivalent pressures and the liquid needed to operate the hydrostatic heating apparatus. The liquid flow path 55 is down the inlet column 45 through the aseptic heating zone 40 and up the exit column 50. In the currently preferred embodiment of the present invention, the hydrostatic pressure means is open to atmospheric pressure, although the columns themselves may be covered to provide for protection from contamination. The cover may or may not be sealed. If sealed, the internal pressure can be equalized to the ambient pressure or a predetermined pressure by use of pressure relief valves and/or pressure compensating passages in the inlet column 45 and exit column 50 of the housing.

The heater 25 can be a standard steam or boiler type heater, a radio-frequencies source, a microwave source, or electric element type heater. The heater 25 is located along the enclosed chamber 10 at the aseptic heating zone 40, and may also extend up onto the inlet column 45 and exit column 50. In one embodiment of the invention the heater extends along the enclosed chamber 10 and an additional 4 meters up the bottom portion of the inlet column 45 and exit column 50. Alternatively, the liquid is heated before it is introduced into the inlet column 45, or pre-heated while it is in the inlet column 45. The liquid can be heated or pre-heated by introducing steam into the liquid column 45, but any number of other heating methods can also be used. There are many combinations of transporting means speed (FIG. 4, FIG. 5), liquid temperature in the inlet column 45, liquid temperature in the aseptic heating zone 40, and length and position of the heater 25 which can provide the desired heating results.

In another aspect of the present invention, the liquid level 60 in the inlet column 45 and exit column 50 is at least about 14.24 meters. Included in this aspect is the use of water as the hydrostatic liquid. The boiling point of water at 1 atmosphere of pressure (atm) is 100 degrees Centigrade. By providing the 14.24 meters of liquid, the pressure is increased by 1.38 atm at the bottom of the inlet column 45 and exit column 50 and the aseptic heating zone 40 which is in fluid communication with the bottom of the inlet column 45 and exit column 50, and therefore exposed to the same pressures. Therefore, the pressure in the aseptic heating zone 40 will be approximately 2.38 atm (35 psi). This will correspondingly increase the boiling point of the liquid at this point to 126 degrees Centigrade.

It is generally accepted by those in the field that an exposure of a low acid food product to a heat treatment of 121.5 degrees Centigrade for three minutes (F0=3) will achieve a 12 D reduction in *Clostridium botulinum* and is therefore an acceptable processing time. However, an F0=5 will generally provide an increase in shelf life because this additional exposure time will kill off spoilage spores which are more resistant than *Clostridium botulinum*. Therefore, the hydrostatic method of increasing the boiling point of the cooking liquid above the sterility temperature allows the cooking and sterilization steps to be performed concurrently and in a continuous manner. In keeping with this aspect of the invention, the height of the inlet column 45, the exit column 50, and the liquid level 60 can be increased or decreased such that the associated increase in pressure will increase the boiling point of the liquid to any number of possible scenarios, for example 5, 10, 15, 20 or more degrees.

The hydrostatic heating apparatus can have a separate liquid inlet opening 65 and liquid outlet opening 70 as illustrated. However, it is possible that the liquid inlet opening 65 and liquid outlet opening 70 can be placed at any number of positions either above, below, or at the same level as the product inlet opening 20 and product outlet opening 30 along the inlet column 45 or the exit column 50. It is also possible to combine the product inlet opening 20 with the liquid inlet opening 65. Likewise, the liquid outlet opening 70 can be combined with the product outlet opening 30.

While cooking or heating, a product may release starch or other components into the liquid. Therefore, in order to prevent excess or run-off accumulation of those by-products in the processing liquid, fresh liquid is introduced into the hydrostatic heating apparatus at a predetermined rate. The liquid level and flow rate are adjusted by separately adjusting the amount of liquid flowing in the liquid inlet opening 65 and the amount of liquid exiting the liquid outlet opening 70. In addition, the liquid outlet opening 70 can have a releasing hose, bigger in diameter and placed slightly lower than the liquid inlet opening 65. This configuration forces the liquid to exit without the use of a suction pump. Although this configuration would not require a pump, the use of a pump is an alternative to maintaining a positive liquid flow so as to prevent reverse flow and contamination. Finally, when sterilizing solid non-food products wherein accumulation of food by-products is not a problem, it may be unnecessary to have a liquid outlet. The liquid level is periodically, rather than continuously, adjusted by allowing only sufficient liquid into the liquid inlet 65 as is necessary to replace any liquid volume lost due to evaporation or leakage.

Figure 2:
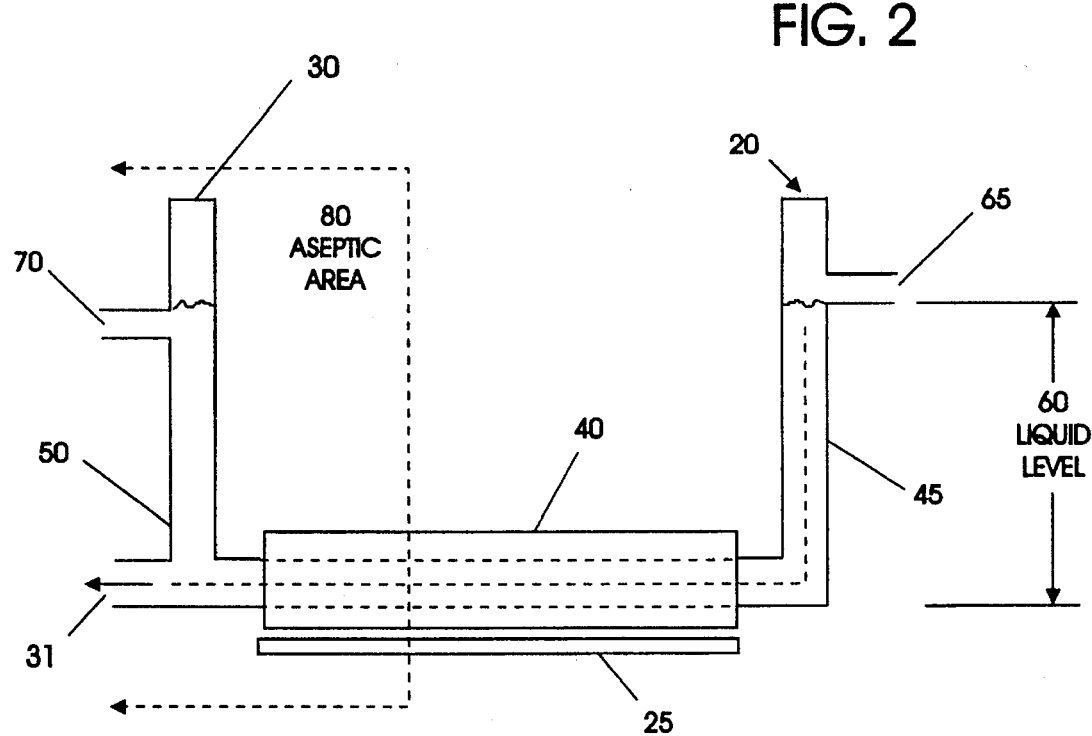
FIG. 2 is a schematic illustration of a hydrostatic heating apparatus with an alternative product outlet opening.

FIG. 2 illustrates an alternative position for the product outlet opening 31. This alternative places the product outlet opening 31 at the bottom portion of the exit column 50 which is below the liquid outlet opening 70 and within the liquid level 60. After the particulate product is cooked and/or sterilized, the transporting means (FIG. 4, FIG. 5, FIG. 9) transports the particulate product out through a sealed product outlet opening 31. The seal uses an o-ring configuration, or other sealing mechanism to prevent fluid loss through the product outlet opening 31.

Figure 3:
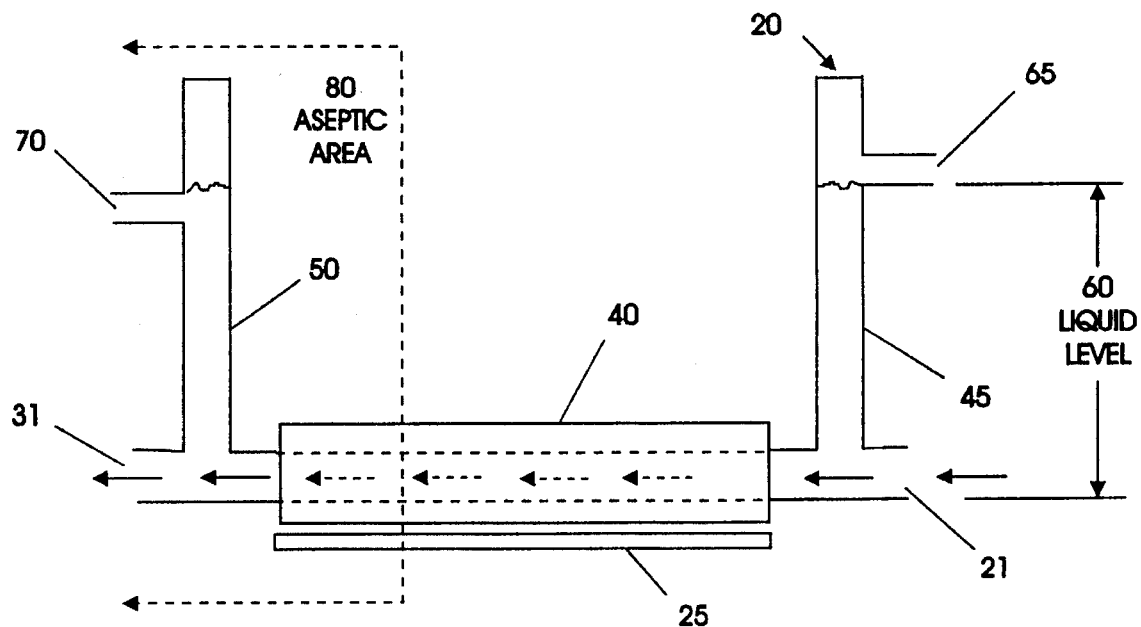
FIG. 3 is a schematic illustration of a hydrostatic heating apparatus with an alternative product inlet and outlet opening.

FIG. 3 illustrates an additional alternative for the placement of the product inlet opening 21. This alternative places the product inlet opening 21 at the bottom portion of the inlet column 45 below the liquid inlet opening 65. The transporting means transports the particulate product from a product inlet opening 21 and through the aseptic heating zone 40. Upon completion of the cooking and/or sterilization process step, the transporting means passes the particulate product out the product outlet opening 31. Both openings are sealed by the use of an o-ring, or through any other sealing mechanism that prevents fluid loss through the product inlet opening 21 or outlet opening 31.

Figure 4:
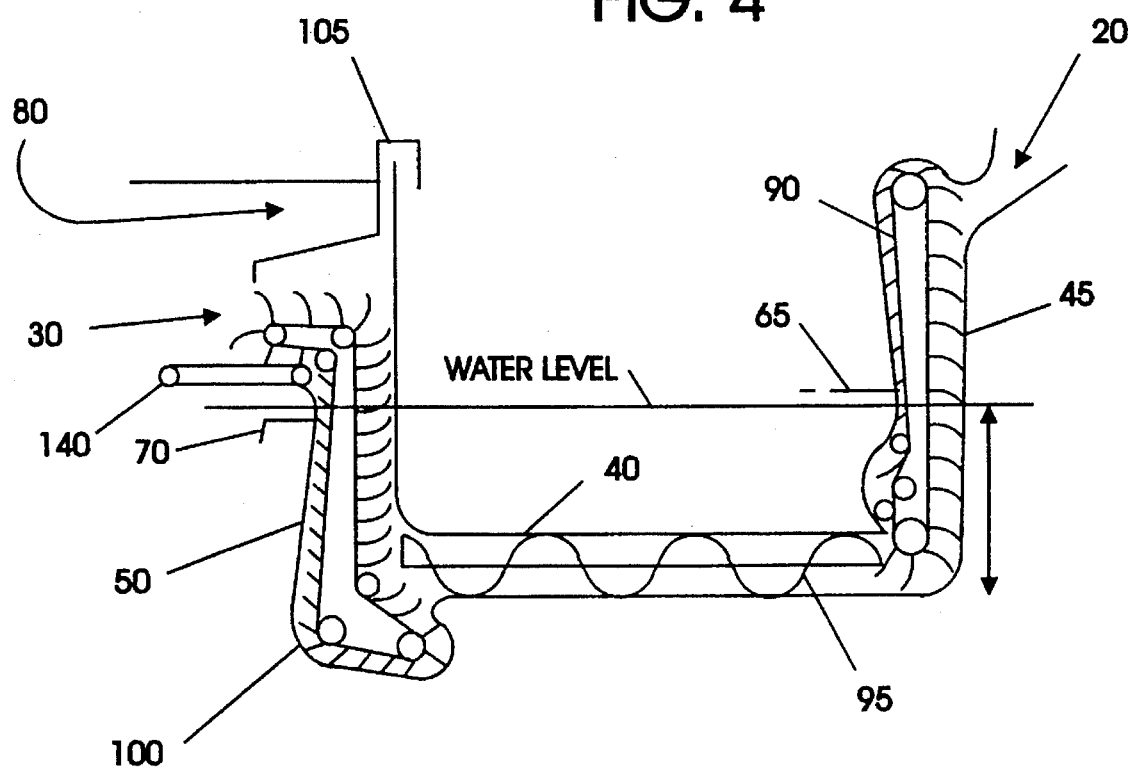
FIG. 4 is a schematic illustration of a transporting means for a hydrostatic heating apparatus.

FIG. 4 illustrates one alternative for a transporting means for transporting a particulate product from the product inlet opening 20 to the bottom of the inlet column 45 into the aseptic heating zone 40 and finally into the exit column 50 and out of the product outlet opening 30. Generally the particulate product is released at a constant rate to the product inlet opening 20. An inverse elevator 90 shaped to collect the particulate product and force it down the inlet column 45 transports the product to the entry of the aseptic heating zone 40. One of many possibilities is to have the inverse elevator 90 be an inverse bucket elevator with drainage openings which allow the particulate product to be contained and moved down through the liquid in the inlet column 45. At the bottom of the inlet column 45, a screw conveyor 95 collects the particulate product and transports it at a predetermined speed through the aseptic heating zone 40 and delivers the particulate product to the bottom of the exit column 50. An exit elevator 100 transports the particulate product to the product outlet opening 30. One alternative for the exit elevator 100 is a bouncing bucket type elevator with drainage openings which helps prevent food particulate products from sticking to each other or the bucket while being transported as well as allows the container to drain the liquid from the particulate product. Subsequently, the particulate product is transported to an aseptic area 80 and released through the product outlet opening 30. Because of the positive flow in the aseptic area 80 towards a vapor release valve 105 (or other vapor release mechanism) a local vacuum is created which allows moisture to be removed from the particulate product and also allows part of the heat in the particulate product to be absorbed by the environment due to the thermal gradient in the system. In this transporting means configuration the separate transporting mechanisms with their associated conventional return means act to maintain the aseptic condition of the aseptic area 80 since the individual return means are individually contained within their respective areas in the apparatus. In the present invention, the transporting means described includes at least one conveyor or elevator. The conveyor can be a screw, drag, cable, disk, bucket, or other such mechanism. The term "screw conveyor" includes, but is not limited to, left or right hand configurations, and single, twin, or multiple screw conveyor configurations. The components described above and and other such mechanisms that serve the same purpose yield a transporting means and can be interchanged in any number of alternative configurations. In one preferred embodiment, a single cable conveyor serves as the transporting means for transporting the particulate product from the inlet opening to the outlet opening.

FIG. 5 shows a continuous conveyor alternative for the transporting means and return means. The conveyor 43 can be a screw, drag, cable, disk, bucket, or other such mechanism. The continuous path requires a separate loop to return the conveyor 43 back to the initial starting point at the product inlet opening 20. The particulate product is introduced at a product inlet opening 20 and the conveyor 43 transports the particulate product in the liquid down the inlet column 45, through the aseptic heating zone 40, up the exit column 50, and finally out the product outlet opening 30. The return loop takes the conveyor 43 back down a first return column 110 through a return aseptic heating zone 41 and finally back up a second return column 115 until the continuous conveyor 43 has returned to its initial position. In order to ensure that the return loop does not introduce contaminants in the aseptic area (FIG. 1 80), the conveyor 43 is returned via the return aseptic heating zone 41. The return aseptic heating zone 41, like the aseptic heating zone 40, contains the hydrostatic liquid and is heated by the heater 25 to a predetermined temperature. Thus, the return heating aseptic zone 41 heats the return loop to maintain sterility. The input loop and the return loop can be reversed with no effect on the function of the invention. In addition, the input loop and return loop can be placed in any number of alternative and positions, such as top to bottom and side by side, that achieve the same purpose.

The columns are made out of stainless steel, but any non-reactive material that can meet the temperature requirements can be used. Currently, there are are several commercial conveyor systems that can be modified to meet the transporting means and return means specifications. For example, the READYBUILT™ or RB™ conveyors, the FLOVEYOR™ conveyor, or the ENTECON™ conveyor system. The alternative product inlet opening (FIG. 3 21) and alternative product outlet opening (FIG. 2 31, FIG. 3 31) configuration can also be used with some modification of the continuous conveyor system discussed above.

Figure 6:
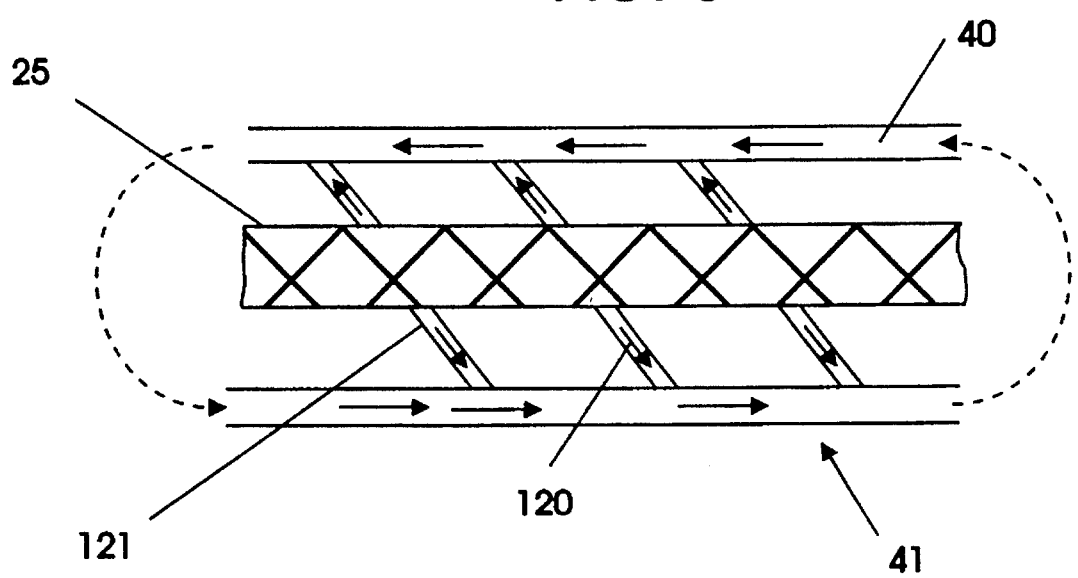
FIG. 6 shows a cross-sectional view of a return means for the transporting means shown in FIG. 5.

FIG. 6 shows an additional feature that may be used to help insure sterility in the return means. The return aseptic heating zone 41 is in fluid communication with the aseptic heating zone 40 by cross feed lines 120. The cross feed lines 120 fluidly connect the aseptic heating zone 40 with the return aseptic heating zone 41. The cross feed lines 120, the aseptic heating zone 40, and the return aseptic heating zone 41 contain liquid that is heated to a predetermined temperature by the heater 25, which either contacts the liquid or indirectly heats the liquid. In one aspect of the invention, the heater 25 heats an element which is placed between, above, or below the aseptic heating zone 40 and the return aseptic heating zone 41. In a preferred aspect, the heating element is non-metallic and is heated using microwave energy. The heating element is below the aseptic heating zone 40 and the return aseptic heating zone 41 so that more surface area is available for irradiation. An additional advantage of this aspect is that heat rises and this phenomenon helps assure the aseptic heating zone 40 and the return aseptic heating zone 41 are provided with hot liquid through the cross feed lines 120. The cross feed lines 120 may have filters 121 to prevent the particulate product from backing into the cross feed lines 120. The cross feed lines 120 are placed such that they are at a sharp angle from the liquid flow path of the conveyor. When using a transporting means that does not include a continuous conveyor system, and therefore does not have a separate return line, the cross feed lines 120 fluidly connect the heater 25 and the aseptic heating zone 40 and thereby heat the liquid in the aseptic heating zone 40.

Figure 7:
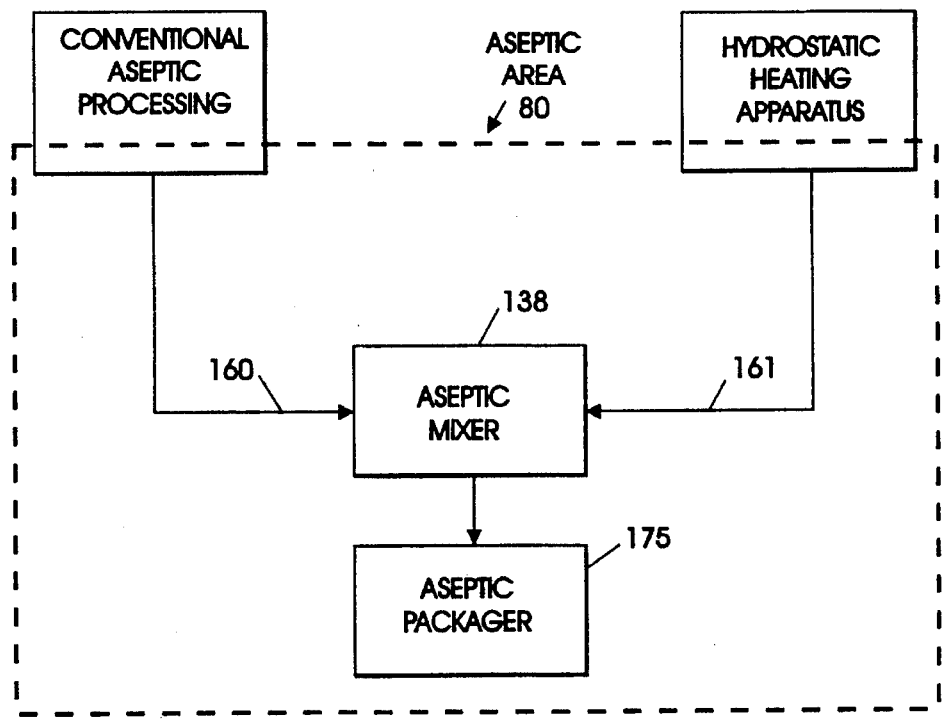
FIG. 7 is a flow diagram of a combination liquid product line and particulate product line with a hydrostatic heating apparatus.

FIG. 7 shows a flow diagram of a combination product line. The liquid product line 160 is aseptically processed according to conventional means. The aseptic liquid product is pumped into an aseptic mixer 138 (FIG. 8) where it is combined with an aseptic particulate product line 161 which has been cooked and/or sterilized by the hydrostatic heating apparatus discussed above. The combination product is then discharged into an aseptic packager 175.

FIG. 8 is a perspective view of an aseptic mixer. After the aseptic particulate product line exits the product outlet opening (FIG. 1 40), the particulate product is conveyed by conveyor 140 (also shown in FIG. 4) to a mixer particulate product inlet opening 146. The particulate product moves against the point of at least one separator 142 which is shaped in a wedge form. The particulate product line then forms at least two lines that drop through the mixing channel particulate product entry opening 150 and into the attached corresponding mixing channels 147 in order to obtain a combination liquid and particulate product mixture. The conventionally processed aseptic liquid product line is pumped into at least one of a multiplicity of liquid product inlet openings 144. The liquid product line then enters the mixing channels 147 through the mixing channel liquid product entry openings 149. The liquid product line and the particulate product line are then combined and fall or slide to the mixer exit opening 148 which is connected to an aseptic fill and packaging area.

FIG. 9 illustrates a cross sectional view of a number of alternative transporting means for transporting the particulate product within the enclosed chamber.

In FIG. 9A a screw conveyor 11 in the inlet column 45 takes the particulate product and submerges the particulate product in liquid while taking the particulate product down to a second screw conveyor 12 in the aseptic heating zone 40. A bucket elevator or belt conveyor 13 in the exit column 50 delivers the particulate product to the product outlet opening FIG. 9B uses one continuous screw conveyor 14 while FIG. 9C uses three separate screw conveyors 11, 12, and 15. There are any number of conveyors and equivalents that would transport the particulate product such as but not limited to screw, drag, cable disk or bucket conveyor configurations. The the inlet column 45 and exit column 50 can be reversed and yield the same results. In addition, the conveyors can be arranged in any number of alternative variations within the enclosed chamber of the apparatus.

In one embodiment of the present invention, a solid product such as macaroni to be both cooked and sterilized enters the apparatus at a product inlet opening 20 (FIG. 2 item 20, FIG. 3 item 21). The macaroni is then immersed in a liquid, particularly water in the inlet column (FIG. 1 45) and transported (FIG. 4 and FIG. 5) while suspended in the water through the aseptic heating zone 40, and is delivered to the aseptic area (FIG. 1 80), and the product outlet opening (FIG. 1 30, FIG. 2 31, FIG. 3 31). The liquid level is approximately 14.24 meters which places approximately 2.38 atmospheres (atm) of pressure on the liquid in the aseptic heating zone 40. The macaroni is processed such the residence time at 121.5 degrees Centigrade meets the Food and Drug Administration (FDA) requirements for sterility. For example, to reach an F0=5 result, the macaroni is immersed in 121.5 degree liquid in the aseptic heating zone (FIG. 1 40) for a period of five minutes. This allows the macaroni to be cooked and sterilized while it is transported in the heated liquid in the aseptic heating zone 40. The macaroni is then transported to the aseptic mixer (FIG. 7 138) where it is combined with a commercially available and conventionally processed aseptic cheese sauce. The combination product is then aseptically filled and packaged.

In another embodiment of the present invention, a semi-solid product, peas, which are to be both cooked and sterilized, enters the apparatus at a product inlet opening 20 (FIG. 2 item 20, FIG. 3 item 21). The transporting means takes the peas and immerses them in a liquid such as water in the inlet column 45 and transports them (FIG. 4, FIG. 5, FIG. 9) in the water through the aseptic heating zone 40, and delivers them to the aseptic area (FIG. 1 80), and out of the product outlet opening 30 (FIG. 2 31, FIG. 3 31). The peas are then transported to an aseptic packaging area or are mixed in accordance with the combination product process discussed above.

In yet another alternative of the present invention, the hydrostatic heating apparatus is used to sterilize a solid product such as medical tools or equipment. This continuous system is more efficient than current autoclave batch applications.

The foregoing examples are illustrative of the present invention, and are not to be construed as limiting thereof.

The invention is defined by the following claims, with equivalents of the claims to be included therein.

That which is claimed is:

1. A hydrostatic heating apparatus for heating a particulate product in a liquid, said hydrostatic heating apparatus comprising:

an enclosed chamber which is open to atmospheric pressure configured to contain said liquid under hydrostatic pressure, said enclosed chamber having a product inlet opening and a product outlet opening formed therein, and having a heating zone positioned between said product inlet opening and said product outlet opening;

transporting means positioned in said enclosed chamber and extending through said heating zone for transporting said particulate product in said liquid from said product inlet opening through said heating zone and to said product outlet opening;

hydrostatic pressure means operatively associated with said enclosed chamber for maintaining said particulate product in said liquid under pressure in said heating zone; and a heater connected to said enclosed chamber for heating said particulate product in said liquid under pressure in said heating zone.

2. An apparatus according to claim 1, said hydrostatic pressure means comprising at least one inlet column formed on said enclosed chamber for supporting said liquid in a hydrostatic liquid column open to atmospheric pressure, at least one exit column formed on said enclosed chamber for supporting said liquid in a hydrostatic liquid column open to atmospheric pressure;

and with said inlet column and said exit column in fluid communication through said heating zone.

3. An apparatus according to claim 2, configured so that each of said inlet and exit columns has a vertical drop sufficient to elevate the pressure of said liquid in said heating zone.

4. An apparatus according to claim 1, wherein said heater is configured to heat said liquid by contacting said liquid to a heated surface.

5. An apparatus according to claim 1, said transporting means comprising at least one conveyor.

6. An apparatus according to claim 1, said transporting means comprising a conveyor, and wherein said transporting means further comprises a return means operatively associated with said transporting means to return said conveyor from said product outlet opening to said product inlet opening without contaminating said heating zone.

7. An apparatus according to claim 1, said heating zone having a heated portion, said transporting means comprising:

a first elevator for transporting said particulate product down said inlet column to said heated portion;

a conveyor operatively associated with said first elevator for transporting said particulate product from said first elevator through said heated portion; and a second elevator operatively associated with said conveyor for transporting said particulate product from said heated portion to said product outlet opening.

8. An apparatus according to claim 1, said transporting means comprising an elevator for transporting said particulate product down said inlet column to said heated portion.

9. An apparatus according to claim 1, said transporting means comprising a conveyor for transporting said particulate product through said heated portion.

10. An apparatus according to claim 1, said transporting means comprising an elevator for transporting said particulate product from said heated portion to said product outlet opening.

11. An apparatus according to claim 1, said transporting means configured so that its speed and length determines the time said particulate product resides in said heated portion.

12. An apparatus according to claim 2, wherein said enclosed chamber further comprises a liquid inlet opening on said inlet column and a liquid outlet opening on said exit column for adjusting the hydrostatic liquid level in said enclosed chamber.

13. An apparatus according to claim 12, configured so that said product inlet opening is below said liquid inlet opening.

14. An apparatus according to claim 12, configured so that said product outlet opening is below said liquid outlet opening.

15. An apparatus according to claim 12, wherein said enclosed chamber configured so that said product outlet opening is above said liquid outlet opening.

16. An apparatus according to claim 12, said enclosed chamber configured so that said product inlet opening is above said liquid inlet opening.

17. An apparatus according to claim 12, said enclosed chamber configured so that said said product outlet opening is combined with said liquid outlet opening.

18. An apparatus according to claim 12, said enclosed chamber configured so that said product inlet opening is combined with said liquid inlet opening.

19. An apparatus according to claim 2, further comprising a pumping means operatively attached to said outlet column to maintain a positive liquid flow so as to prevent reverse flow and contamination.

20. An apparatus according to claim 1, further comprising a drive means operatively associated with said transporting means for driving said transporting means.

* * * * *